United States Patent
Belef et al.

(10) Patent No.: US 7,842,065 B2
(45) Date of Patent: *Nov. 30, 2010

(54) RAPID EXCHANGE SHEATH FOR DEPLOYMENT OF MEDICAL DEVICES AND METHODS OF USE

(75) Inventors: W. Martin Belef, San Jose, CA (US); Ross S. Tsugita, Mountain View, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1019 days.

This patent is subject to a terminal disclaimer.

(21) Appl. No.: 11/611,272

(22) Filed: Dec. 15, 2006

(65) Prior Publication Data

US 2007/0083216 A1    Apr. 12, 2007

Related U.S. Application Data

(63) Continuation of application No. 10/039,214, filed on Jan. 4, 2002, now Pat. No. 7,169,165.

(60) Provisional application No. 60/262,136, filed on Jan. 16, 2001.

(51) Int. Cl.
*A61M 29/00* (2006.01)
(52) U.S. Cl. ..................................... 606/200
(58) Field of Classification Search ................ 606/113, 606/114, 127, 159, 200
See application file for complete search history.

(56) References Cited

U.S. PATENT DOCUMENTS

| 3,472,230 A | 10/1969 | Fogarty |
|---|---|---|
| 3,952,747 A | 4/1976 | Kimmell, Jr. |
| 3,996,938 A | 12/1976 | Clark, III |
| 4,425,908 A | 1/1984 | Simon |
| 4,643,184 A | 2/1987 | Mobin-Uddin |
| 4,662,885 A | 5/1987 | DiPisa, Jr. |
| 4,706,671 A | 11/1987 | Weinrib |
| 4,723,549 A | 2/1988 | Wholey et al. |
| 4,790,812 A | 12/1988 | Hawkins, Jr. et al. |
| 4,790,813 A | 12/1988 | Kensey |
| 4,794,928 A | 1/1989 | Kletschka |
| 4,857,045 A | 8/1989 | Rydell |
| 4,873,978 A | 10/1989 | Ginsburg |
| 4,886,061 A | 12/1989 | Fischell et al. |
| 4,947,864 A | 8/1990 | Shockey et al. |
| 4,969,891 A | 11/1990 | Gewertz |

(Continued)

FOREIGN PATENT DOCUMENTS

JP     6165820 A    6/1994

(Continued)

*Primary Examiner*—Kevin T Truong
(74) *Attorney, Agent, or Firm*—Crompton, Seager & Tufte LLC (57) ABSTRACT

A rapid exchange sheath comprising an elongate tubular member, a guidewire, and support wire having an expandable filter at a distal end. The guidewire passes through a first opening at a distal end of the tubular member and a second opening a short distance proximal from the distal end. The support wire is received in a lumen of the tubular member, or, in certain embodiments, extends proximally through a third opening a short distance proximal from the distal end. Methods of using the sheaths for deploying and/or exchanging medical device(s) in a patient's vessel are also disclosed.

14 Claims, 13 Drawing Sheets

U.S. PATENT DOCUMENTS

| | | | |
|---|---|---|---|
| 5,011,488 A | 4/1991 | Ginsburg | |
| 5,071,407 A | 12/1991 | Termin et al. | |
| 5,133,733 A | 7/1992 | Rasmussen et al. | |
| 5,160,342 A | 11/1992 | Reger et al. | |
| 5,192,286 A | 3/1993 | Phan et al. | |
| 5,324,304 A | 6/1994 | Rasmussen | |
| 5,329,942 A | 7/1994 | Gunther et al. | |
| 5,370,657 A | 12/1994 | Irie | |
| 5,415,630 A | 5/1995 | Gory et al. | |
| 5,419,774 A | 5/1995 | Willard et al. | |
| 5,462,529 A | 10/1995 | Simpson et al. | |
| 5,531,700 A | 7/1996 | Moore et al. | |
| 5,536,242 A | 7/1996 | Willard et al. | |
| 5,549,626 A | 8/1996 | Miller et al. | |
| 5,662,671 A | 9/1997 | Barbut et al. | |
| 5,669,933 A | 9/1997 | Simon et al. | |
| 5,769,816 A | 6/1998 | Barbut et al. | |
| 5,779,716 A | 7/1998 | Cano et al. | |
| 5,800,457 A | 9/1998 | Gelbfish | |
| 5,800,525 A | 9/1998 | Bachinski et al. | |
| 5,807,398 A | 9/1998 | Shaknovich | |
| 5,814,064 A | 9/1998 | Daniel et al. | |
| 5,833,650 A | 11/1998 | Imran | |
| 5,848,964 A | 12/1998 | Samuels | |
| 5,911,734 A | 6/1999 | Tsugita et al. | |
| 6,066,149 A | 5/2000 | Samon et al. | |
| 6,066,158 A | 5/2000 | Engelson et al. | |
| 6,142,987 A | 11/2000 | Tsugita | |
| 6,152,946 A | 11/2000 | Broome et al. | |
| 6,168,579 B1 | 1/2001 | Tsugita | |
| 6,171,327 B1 | 1/2001 | Daniel et al. | |
| 6,179,861 B1 | 1/2001 | Khosravi et al. | |
| 6,203,561 B1 | 3/2001 | Ramee et al. | |
| 6,206,868 B1 | 3/2001 | Parodi | |
| 6,221,006 B1 | 4/2001 | Dubrul et al. | |
| 6,277,139 B1 | 8/2001 | Levinson et al. | |
| 6,371,969 B1 | 4/2002 | Tsugita et al. | |
| 6,537,294 B1 * | 3/2003 | Boyle et al. | 606/200 |
| 6,605,102 B1 | 8/2003 | Mazzocchi et al. | |
| 7,169,165 B2 * | 1/2007 | Belef et al. | 606/200 |

FOREIGN PATENT DOCUMENTS

| | | |
|---|---|---|
| JP | 11507263 | 6/1999 |
| WO | 96/01591 A1 | 1/1996 |
| WO | 98/50103 A1 | 11/1998 |
| WO | 02/062266 A2 | 8/2002 |

* cited by examiner

RAPID EXCHANGE SHEATH FOR DEPLOYMENT OF MEDICAL DEVICES AND METHODS OF USE

This application is a continuation of U.S. application Ser. No. 10/039,214 filed Jan. 4, 2002 which claims benefit of U.S. Provisional Application Ser. No. 60/262,136 filed Jan. 16, 2001.

FIELD OF THE INVENTION

The present invention relates generally to devices and methods for deploying an endoluminal medical device, e.g., an angioplasty, atherectomy, or stent deployment catheter, to a region of interest within the vessel. More particularly, the invention provides a rapid exchange sheath for deployment of medical devices for directing and/or exchanging "over the wire" medical devices.

BACKGROUND OF THE INVENTION

Treatment of thrombotic or atherosclerotic lesions in blood vessels using an endovascular approach has recently proven to be an effective and reliable alternative to surgical intervention in selected patients. For example, directional atherectomy and percutaneous translumenal coronary angioplasty (PTCA) with or without stent deployment are useful in treating patients with coronary occlusion. Atherectomy physically removes plaque by cutting, pulverizing, or shaving in atherosclerotic arteries using a catheter-deliverable endarterectomy device. Angioplasty enlarges the lumenal diameter of a stenotic vessel by exerting mechanical force on the vascular walls. In addition to using angioplasty, stenting, and/or atherectomy on the coronary vasculature, these endovascular techniques have also proven useful in treating other vascular lesions in, for example, carotid artery stenosis, peripheral arterial occlusive disease (especially the aorta, the iliac artery, and the femoral artery), renal artery stenosis caused by atherosclerosis or fibromuscular disease, superior vena cava syndrome, and occlusive iliac vein thrombosis resistant to thrombolysis.

It is well recognized that one of the complications associated with endovascular techniques is the dislodgment of embolic materials generated during manipulation of the vessel, thereby causing occlusion of the narrower vessels downstream and ischemia or infarct of the organ which the vessel supplies. In 1995, Waksman et al. disclosed that distal embolization is common after directional atherectomy in coronary arteries and saphenous vein grafts. See Waksman et al., American Heart Journal 129(3): 430-5 (1995), incorporated herein by reference. This study found that distal embolization occurs in 28% (31 out of 111) of the patients undergoing atherectomy. In January 1999, Jordan, Jr. et al. disclosed that treatment of carotid stenosis using percutaneous angioplasty with stenting is associated with more than eight times the rate of microemboli seen using carotid endarterectomy. See Jordan, Jr. et al. Cardiovascular surgery 7(1): 33-8 (1999), incorporated herein by reference. Microemboli, as detected by transcranial Doppler monitoring in this study, have been shown to be a potential cause of stroke. The embolic materials include calcium, intimal debris, atheromatous plaque, thrombi, and/or air.

There are a number of devices designed to provide blood filtering for entrapment of vascular emboli. Filters mounted to the distal end of guidewires have been proposed for intravascular blood filtration. A majority of these devices includes a filter which is attached to a guidewire and is mechanically actuated via struts or a pre-shaped basket which deploys in the vessel. These filters are typically mesh "parachutes" which are attached to the shaft of the wire at the distal end and to wire struts which extend outward in a radial direction at their proximal end. The radial struts open the proximal end of the filter to the wall of the vessel. Blood flowing through the vessel is forced through the mesh thereby capturing embolic material in the filter. These devices are self-directing and can be placed intravascularly. However, one major disadvantage associated with the current devices is that the steerability of the guidewire may be altered as compared to the conventional guidewires due to the size of the filter. The guidewire may bend, kink, and/or loop around in the vessel, making insertion of the filter through a complex vascular lesion difficult.

During endovascular procedures, it is not uncommon to exchange one endovascular device for another over the guidewire. However, the guidewire position is often lost or compromised during the exchange of devices. For example, during coronary revascularization, it is often required to exchange of one guide catheter for another guide catheter possessing different qualities, e.g., a larger diameter guide to deliver a specialized angioplasty device, a smaller diameter guide to prevent deep intubation and/or pressure damping, a different guide shape, or a guide catheter containing side holes. It is known that there are few interventional maneuvers as challenging as attempting to maintain distal guidewire access while trying to exchange one guiding catheter for another without compromising the guidewire position.

What is needed are rapid exchange sheaths which can be advanced over a guidewire and carry an endoluminal medical device to a region of interest and can thereafter be removed from a patient's vessel without requiring a large proximal guidewire segment extending out of the patient's vessel. Existing devices are inadequate for this purpose.

SUMMARY OF THE INVENTION

The present invention provides rapid exchange sheaths for deployment and exchange of various endoluminal medical devices, including an angioplasty catheter, a stent-deployment catheter, an atherectomy catheter, an intravascular ultrasound catheter, a guidewire, a filter catheter, a filter guidewire, a support wire, a support wire having a filter, and an aspiration catheter. Any of these devices can be exchanged for any other of these devices, or even for the same device, as in the exchange of one guidewire for another guidewire. In a first embodiment, the sheath comprises an elongate tubular member which has a lumen communicating with a proximal end and a distal end. The sheath has a first opening at the distal end adapted for passage of a guidewire, support wire, and a medical device, and a second opening positioned a short distance from the distal end (i.e., skive). The sheath includes a guidewire which passes through the first opening, the lumen of the tubular member, and the second opening. The sheath may also include a support wire which has a proximal end, a distal end, and an expandable filter mounted on the distal end. The filter and the support wire, which is adapted to receive an endoluminal medical device, are positioned within the lumen of the tubular member.

In certain embodiments, the filtering device, e.g., a parachute, basket, or scroll, comprises on an expandable frame, and a mesh disposed over the frame. The filtering device may include an inflation seal for achieving better contact with the vascular walls. The construction and use of a filter mesh have been thoroughly discussed in earlier applications including Barbut et al., U.S. application Ser. No. 08/533,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, Barbut et al., U.S. Pat. No. 5,769,816, Barbut et al., U.S. application Ser. No. 08/645,762, filed May 14, 1996, Maahs, U.S. Pat. No. 5,846,260, and, Barbut et al., U.S. Pat. No. 5,662,671, and the contents of each of these prior disclosures are expressly incorporated herein by reference in their entirety.

In another embodiment, the rapid exchange sheath comprises an elongate member which includes a third opening a short distance proximal the first opening. The guidewire is passed through the first and second openings, and the support wire is passed through the first and third openings. In certain embodiments, the elongate member has a lumen which communicates with the proximal and distal ends and is adapted for infusion and aspiration of fluid or blood. In certain embodiments, the proximal end of the tubular member includes a hemostatic valve for preventing back flow of blood during insertion into a vessel.

The methods of the present invention are useful for deploying a medical device within a body cavity and for protecting a patient from embolization during an endovascular procedure. The rapid exchange sheaths can be inserted to deploy medical instruments within the coronary artery, aorta, common carotid artery, external and internal carotid arteries, brachiocephalic trunk, middle cerebral artery, basilar artery, subclavian artery, brachial artery, axillary artery, iliac artery, renal artery, femoral artery, popliteal artery, celiac artery, superior mesenteric artery, inferior mesenteric artery, anterior tibial artery, posterior tibial artery, and all other arteries carrying oxygenated blood. The sheaths can be used prophylactically in patients with hypercoagulable state, including protein C or protein S deficiency, to deploy a filter and prevent pulmonary embolism. It can also be used during an endovascular procedure to gain access and to prevent distal embolization of thrombi and/or foreign bodies in the venous circulation, including the superior vena cava, inferior vena cava, external and internal jugular veins, brachiocephalic vein, pulmonary artery, subclavian vein, brachial vein, axillary vein, iliac vein, renal vein, femoral vein, profunda femoris vein, great saphenous vein, portal vein, splenic vein, hepatic vein, and azygous vein.

In a first method of treating an endovascular lesion using the rapid exchange sheaths having two openings in the tubular member described above, the guidewire is inserted through an incision on a peripheral vessel, such as the femoral or the subclavian artery/vein, advanced to a region of interest. The proximal end of the guidewire is passed through the first opening, the lumen of the elongate member, and through the second opening. The tubular member is then advanced over the guidewire until it is positioned within a region of interest. An endoluminal medical device, such as an angioplasty catheter, is inserted in the lumen of the tubular member and advanced until it is positioned within the region of interest. After the medical device is deployed in the vessel, the guidewire may be withdrawn and the tubular member may be withdrawn.

In another method, after insertion of the guidewire, the tubular member, which includes a support wire having a filter in a collapsed state, is advanced over the guidewire until it is positioned within a region of interest. The distal end of the support wire is extended beyond the first opening. An endoluminal medical device is inserted over the support wire and advanced until it is positioned within the region of interest. The filter is expanded to capture embolic material, such as calcium, thrombi, atheromatous plaque, gas, bubbles, and/or tissue debris, generated during the endovascular procedure.

In another method using the elongate member which includes first, second, and third openings, a guidewire is first advanced to a region of interest within a patient's vessel. The proximal end of the guidewire is passed through the first and second openings of the tubular member. A support wire having a collapsed filter in its distal end is received within a capture sleeve located between the first and third openings, and extends proximally through the third opening. The elongate member is advanced over the guidewire until it is positioned within the region of interest. In certain embodiments, the guidewire and elongate member are then removed, leaving only the support wire in place. An endoluminal device is inserted over the support wire and advanced to the region of interest. When deployment of a second medical device is desired, the first medical device is withdrawn over the support wire and, if the elongate member is still in place, from the lumen of the elongate member, and the second device is inserted over the support wire to position within the region of interest.

It will be understood that there are several advantages in using the rapid exchange sheaths and methods disclosed herein for deployment of medical devices during endovascular procedures. For example, the sheaths (1) provide access over a guidewire to a region of interest within a vessel, (2) allow deployment of a selected endoluminal medical device to a region of interest while safely carried within the sheath, (3) allow removal of the guidewire once the sheath and first endoluminal device are in place, (4) provide for removal of the sheath while avoiding the use of an extended segment of guidewire outside the patient's body, (5) allow use of a support wire as the first endoluminal device to provide distal embolic protection, (6) protect the support wire carrying the filter during its insertion, thereby minimizing bending, kinking, and/or looping around in the vessel, and (7) can be used in adult and pediatric patients.

BRIEF DESCRIPTION OF THE DRAWINGS

FIG. 5D depicts the filter wire of FIG. 8C after removal of the sheath.

DETAILED DESCRIPTION

Figure 1A:
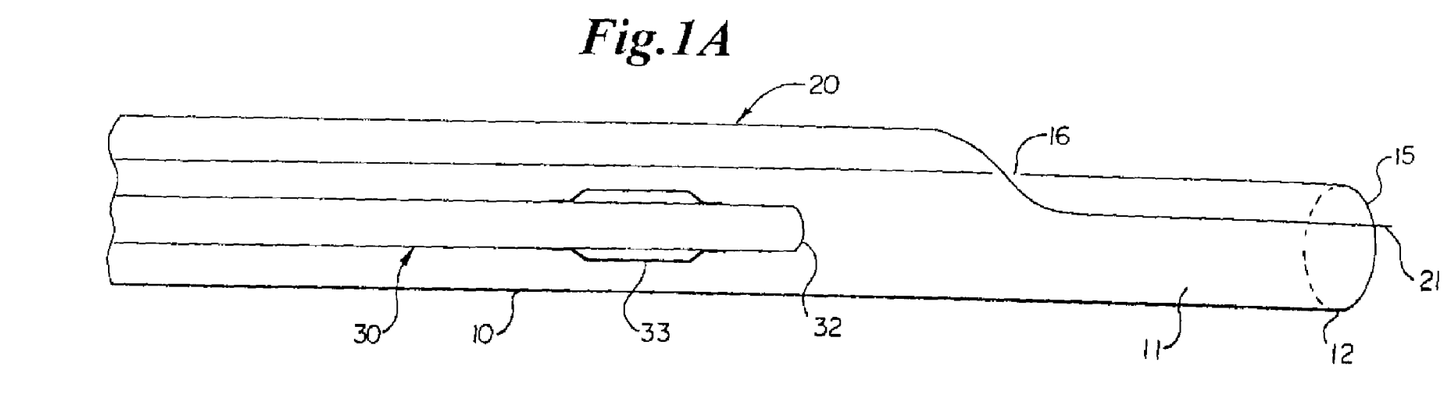
FIG. 1A depicts an embodiment of the rapid exchange sheath for deployment of an angioplasty catheter according to the present invention.

Referring now to the drawings, an embodiment of the rapid exchange sheath for deployment of angioplasty catheter 30 is depicted in FIG. 1A. The sheath comprises elongate tubular member 10 having lumen 111 communicating with a proximal end and distal end 12. Tubular member 10 has first opening 15 at distal end 12, and second opening 16 a short distance proximal to distal end 12. Opening 16 can be located from 1 millimeter to 50 centimeters proximal of openings 15, and at distances of 2, 4, 6, 8, 10, 12, 14, 16, or 18 centimeters proximal of opening 15, or at any other suitable distance. Lumen 11 is adapted to receive an endoluminal medical device, such as angioplasty catheter 30. Angioplasty balloon 33 is mounted on distal end 32 of the angioplasty catheter. Guidewire 20, which has a proximal end and distal end 21, passes through opening 16, lumen 11, and opening 15 of tubular member 10.

Figure 1B:
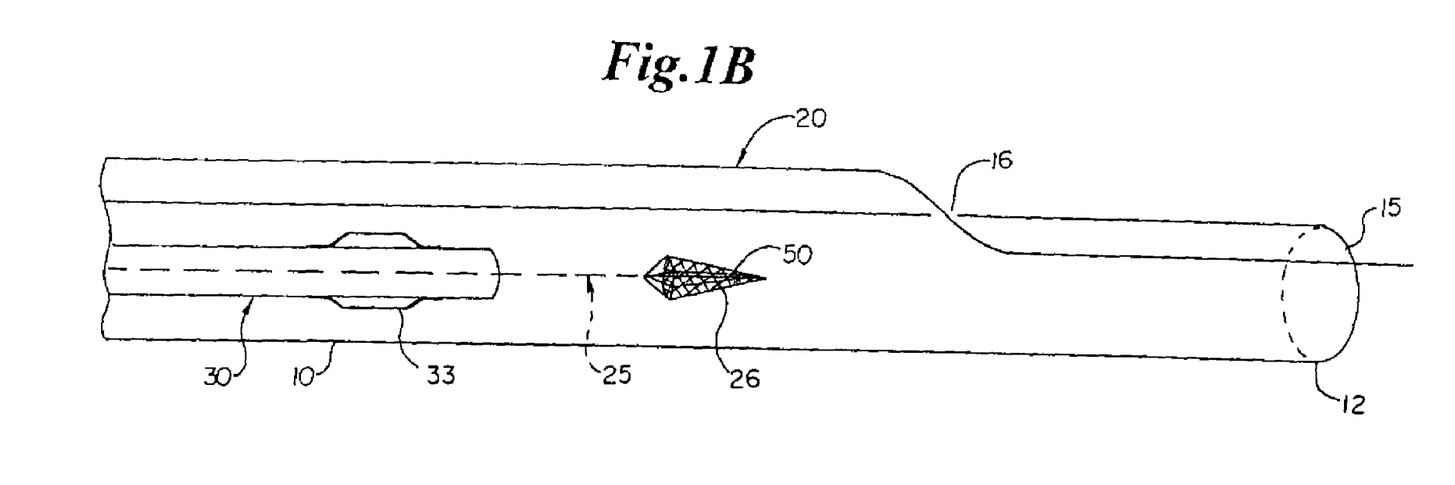
FIG. 1B depicts another embodiment of the rapid exchange sheath carrying a support wire in its lumen.

Another embodiment of the rapid exchange sheath for deployment of angioplasty catheter 30 is shown in FIG. 1B. The sheath includes support wire 25 having expandable filter device 50 mounted on distal end 26. The support wire is adapted to receive angioplasty catheter 30.

Figure 2A:
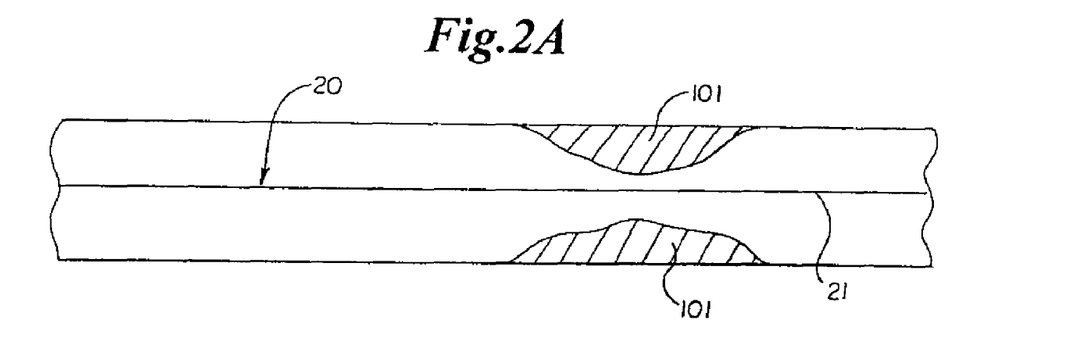
FIG. 2A depicts a guidewire inserted in a vessel.
Figure 2B:
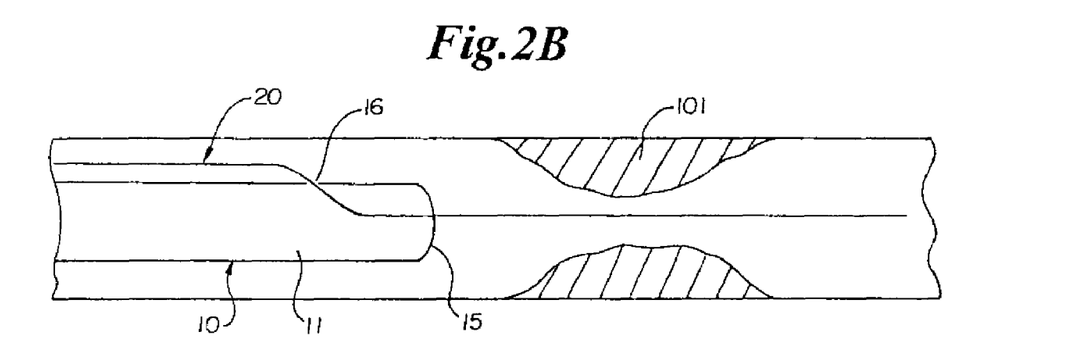
FIG. 2B depicts a rapid exchange sheath inserted over the guidewire of FIG. 2A.
Figure 2C:
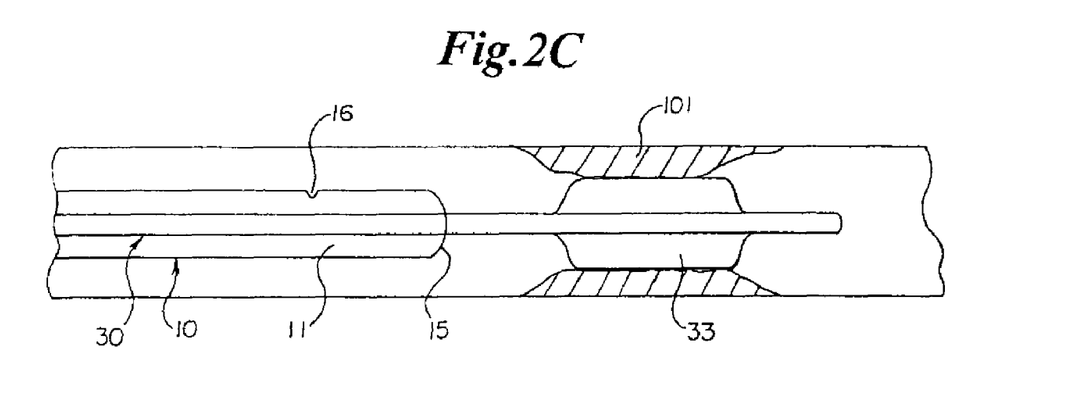
FIG. 2C depicts an angioplasty catheter deployed within a region of interest using the rapid exchange sheath of FIG. 1A.

In using the rapid exchange sheath of FIG. 1A for deployment of a medical device, guidewire 20 is first inserted through an incision on a peripheral artery, such as the femoral or the subclavian artery, and into a region of interest as depicted in FIG. 2A. Distal end 21 of guidewire 20 is advanced past atheromatous lesion 101. The proximal end of guidewire 20 is passed through first opening 15, lumen 1, and second opening 16 of tubular member 10 as depicted in FIG. 2B. The tubular member is then advanced over the guidewire until it is positioned proximal to lesion 101. Guidewire 20 may be removed from the vessel. A medical device, such as angioplasty catheter 30 is inserted into lumen 11 and advanced until it is positioned within lesion 101 as depicted in FIG. 2C. Alternatively, angioplasty catheter 30 is inserted within lumen 11 of tubular member 10 before advancing the tubular member over the guidewire. Angioplasty balloon 33 is then inflated against lesion 101 to re-establish lumenal patency.

Figure 3A:
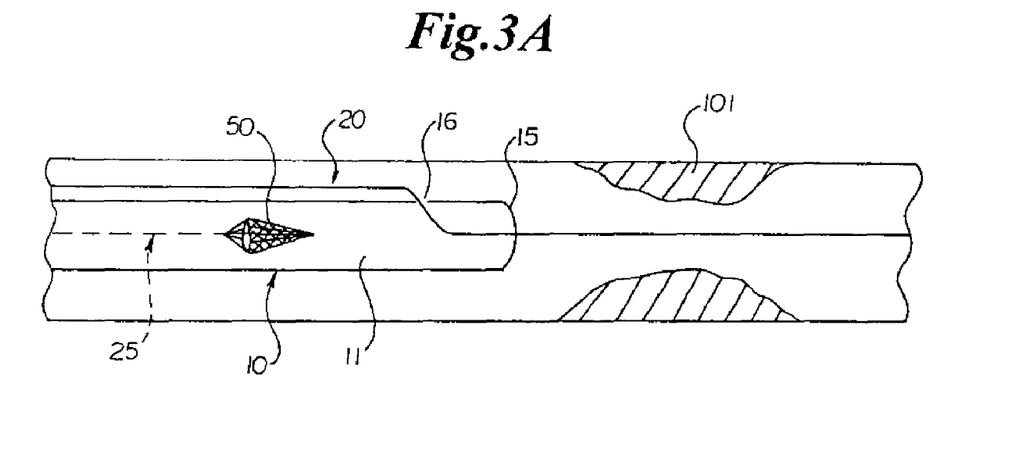
FIG. 3A depicts the rapid exchange sheath of FIG. 1B inserted in a vessel.
Figure 3B:
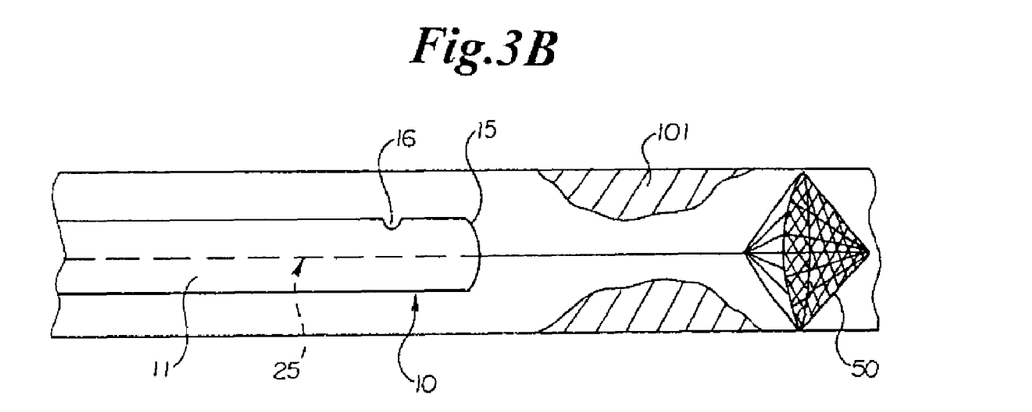
FIG. 3B depicts a filter of FIG. 2A deployed downstream a region of interest.
Figure 3C:
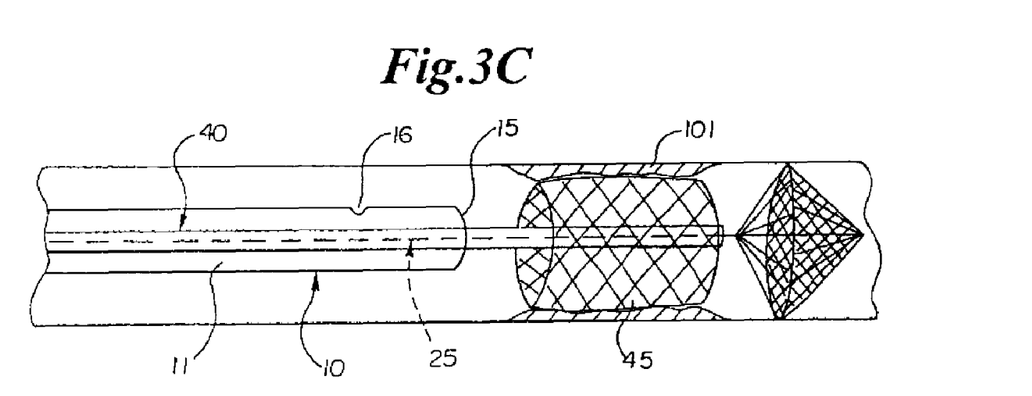
FIG. 3C depicts a stent deployment catheter deployed within a region of interest using the rapid exchange sheath of FIG. 1B.

In using the rapid exchange sheath of FIG. 1B for deployment of a medical device, the guidewire is inserted into a patient's vessel and advanced to a region of interest. The proximal end of guidewire 20 is inserted through first opening 15, lumen 11, and second opening 16 of tubular member 10 as depicted in FIG. 3A. Support wire 25, which carries filter 50 in a collapsed state, is inserted in lumen 11, and advanced proximal to lesion 101. Alternatively, support wire 25 is positioned within lumen 11 before advancing tubular member 10 over guidewire 20. In FIG. 3B, filter 50, which includes a porous mesh, is advanced distal to lesion 101 and expanded to capture embolic material, e.g., calcium, atheromathous plaque, thrombi, and tissue debris, generated during the endovascular procedure. Guidewire 20 is removed before or after positioning filter 50. Stent deployment catheter 40, which has stent 45 mounted on its distal end, is inserted and advanced over support wire 25 to position within lesion 101. Stent 45 is placed in a collapsed state to facilitate insertion into lumen 11, and is placed in an expanded state by an actuating mechanism in the proximal end of the catheter. In certain embodiments, the stent is made of a shape-memory material, e.g., nitinol, which allows self-expansion of the stent in body temperature. In other cases the stent is expanded by inflating a balloon.

By way of example, when a filter as disclosed herein is intended for use in the aorta, the area of the mesh required for the device is calculated from Bernoulli's equation as described in our earlier applications including Barbut et al., U.S. application Ser. No. 08/533,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, Barbut et al., U.S. Pat. No. 5,769,816, Barbut et al., U.S. application Ser. No. 08/645,762, filed May 14, 1996, Maahs, U.S. Pat. No. 5,846,260, and, Barbut et al., U.S. Pat. No. 5,662,671, and the contents of each of these prior disclosures are expressly incorporated herein by reference in their entirety.

In an embodiment of the filter that is to be used in an artery, such as the carotids or the aorta, mesh with dimensions within the following ranges is desirable: mesh area is 0.004-5 in$^2$, more preferably 0.007-4 in$^2$, more preferably 0.010-3 in$^2$, more preferably 0.015-2 in$^2$, more preferably 0.020-1 in$^2$, more preferably 0.025-0.076 in$^2$; mesh thickness is 60-280 µm, more preferably 70-270 µm, more preferably 80-260 µm, more preferably 90-250 µm, more preferably 100-250 µm, more preferably 120-230 µm, more preferably 140-210 µm; thread diameter is 30-145 µm, more preferably 40-135 µm, more preferably 50-125 µm, more preferably 60-115 µm, more preferably 70-105 µm, and pore size is 500 µm or less, more preferably 400 µm or less, more preferably 300 µm or less, more preferably 200 µm or less, more preferably 100 µm or less, more preferably 50 µm or less and usually larger than at least a red blood cell. In a preferred embodiment of the invention, mesh area is 2-8 in$^2$, mesh thickness is 60-200 µm, thread diameter is 30-100 µm, and pore size is 50-300 µm. In a further preferred embodiment of the invention, mesh area is 3-5 in$^2$, mesh thickness is 60-150 µm, thread diameter is 50-80 µm, and pore size is 100-250 µm. In other embodiments, the filter comprises a thin film laser cut with holes to allow blood flow. Typical dimensions include pore size of 20-500 μm, a thickness of 0.00001-0.003 inches, and area approximately the same as for meshes described above.

Once appropriate physical characteristics are determined, suitable mesh can be found among standard meshes known in the art. For example, polyester meshes may be used, such as meshes made by Saati Corporations and Tetko Inc. These are available in sheet form and can be easily cut and formed into a desired shape. In a preferred embodiment, the mesh is sonic welded or adhesive bonded into a cone shape. Other meshes known in the art, which have the desired physical characteristics, are also suitable. Anticoagulants, such as heparin and heparinoids, may be applied to the mesh to reduce the chances of blood clotting on the mesh. Anticoagulants other than heparinoids also may be used, e.g., ReoPro (Centocor). The anticoagulant may be painted or sprayed onto the mesh. A chemical dip comprising the anticoagulant also may be used. Other methods known in the art for applying chemicals to mesh may be used.

Figure 4:
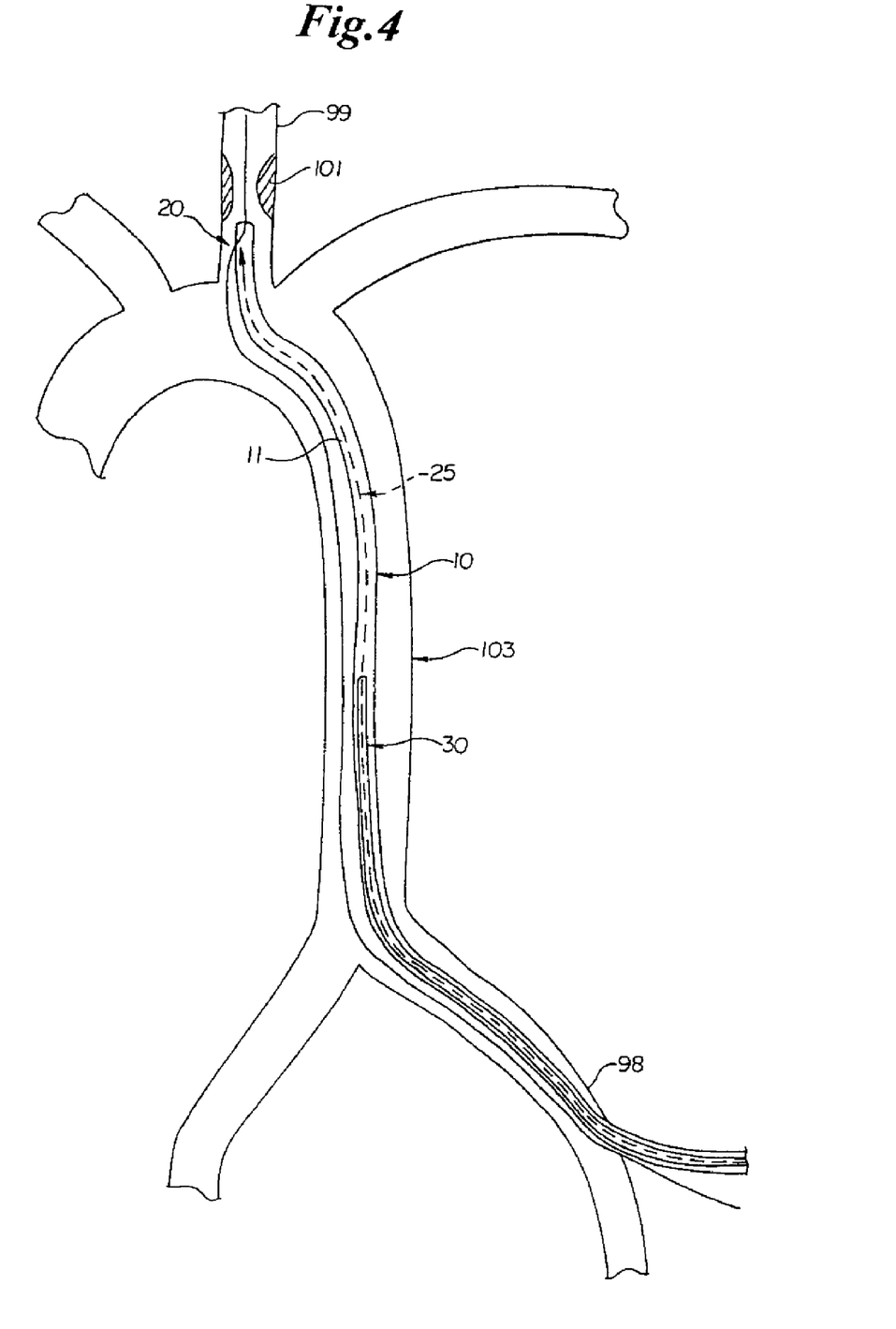
FIG. 4 depicts the rapid exchange sheath of FIG. 1B inserted through left femoral artery to treat a vascular lesion in the left common carotid artery.

The rapid exchange sheaths disclosed herein are useful in treating occlusion vascular lesions in various arteries and veins. For example, in removing atheromatous plaque in left common carotid artery 99 as depicted in FIG. 4, the rapid exchange sheath of FIG. 1B is inserted through an incision on left femoral artery 98. After insertion of guidewire 20, tubular member 10 is inserted over the proximal end of the guidewire and advanced proximal to lesion 101 via descending aorta 103. Support wire 25, which carries filter 50 in a collapsed state, is then inserted in lumen 11 of tubular member 10. Alternatively, support wire 25 is positioned within lumen 11 prior to advancing tubular member 10 over guidewire 20. An endovascular device, such as angioplasty catheter 30, is inserted over support wire 25 before or after removal of tubular sheath 10.

Figure 5A:
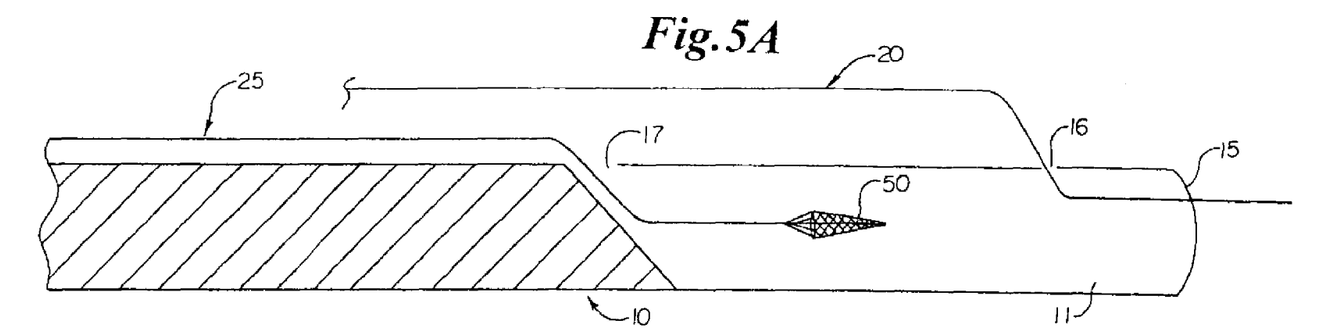
FIG. 5A depicts another embodiment of the rapid exchange sheath having a third opening on an elongate member.
Figure 5B:
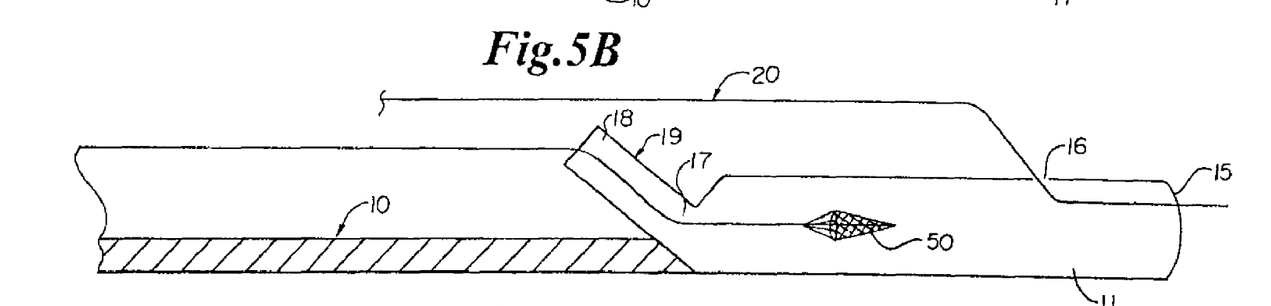
FIG. 5B depicts another embodiment of the rapid exchange sheath having a tubular member extending proximally from the third opening.
Figure 5C:
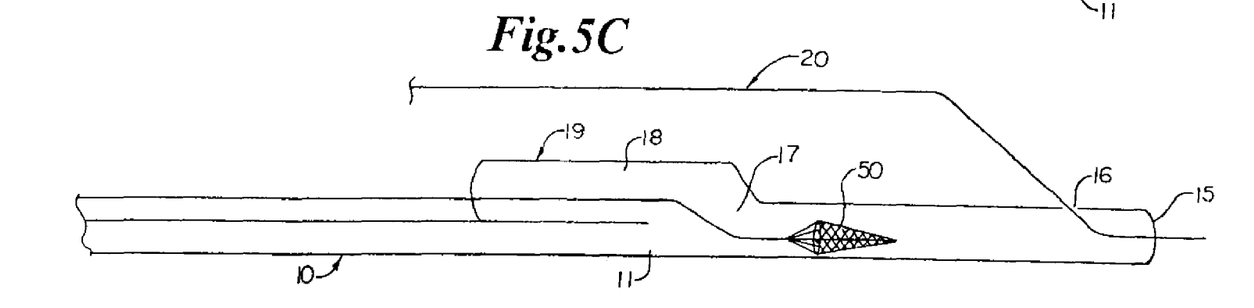
FIG. 5C depicts another embodiment of the rapid exchange sheath having a proximal lumen adapted for infusion and aspiration.

FIGS. 5A, 5B, and 5C depict other embodiments of a rapid exchange sheath having third opening 17 a short distance proximal of first and second openings 15 and 16. Guidewire 20 is inserted through second opening 16, lumen 11 and first opening 15. In FIG. 5A, support wire 25 is backloaded through opening 15 and then opening 17, or is inserted through third opening 17, lumen 111 can and eventually be advanced through first opening 15. In FIGS. 5B and 5C, the sheaths include second tubular member 19 that extends proximal third opening 17. In these two embodiments, support wire 25 is insertable through lumen 18 of second tubular member 19, third opening 17, lumen 11, and can be advanced through first opening 15, or can be backloaded in a reverse manner. In FIGS. 5A and 5B, each embodiment comprises elongate member 10 which has lumen 11 in the distal region. Lumen 111 communicates with third opening 17 proximally and first opening 15 distally. In contrast, the embodiment in FIG. 5C comprises elongate tubular member 10 having lumen 11 communicating with a proximal end (not shown), third opening 17, lumen 18 of second tubular member 19, and distal opening 15. Lumen 11 permits infusion and aspiration of fluid and/or air.

Figure 6A:
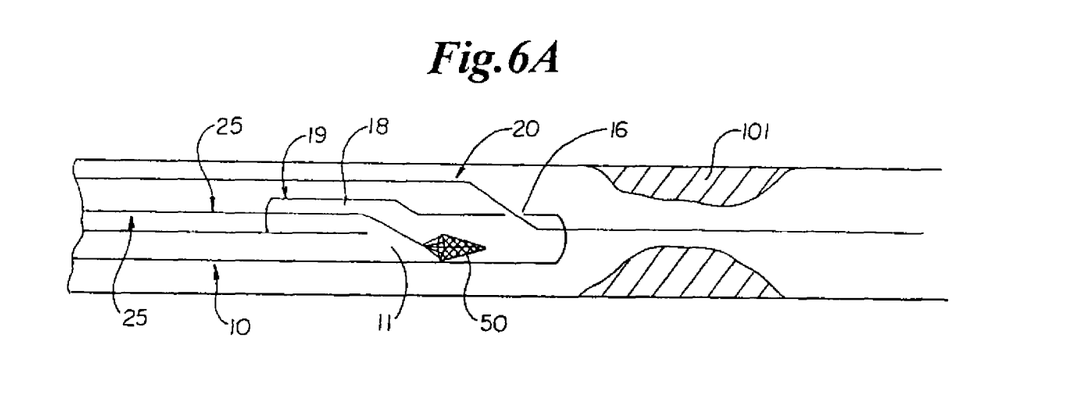
FIG. 6A depicts the rapid exchange sheath of FIG. 5C inserted into a vessel.
Figure 6B:
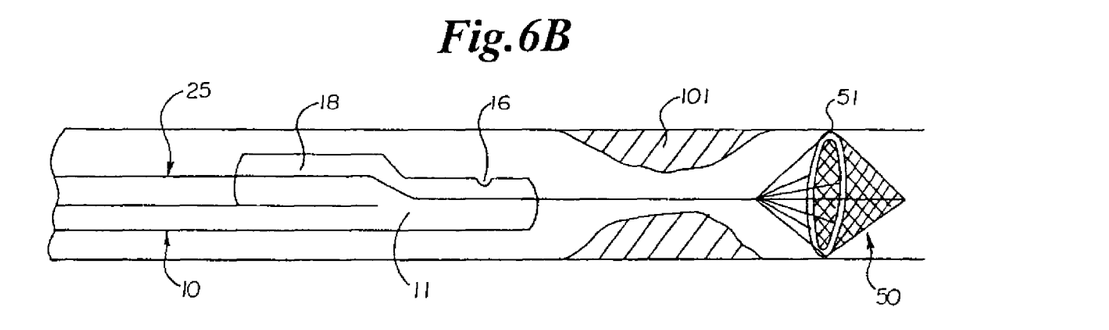
FIG. 6B depicts deployment of a filter downstream the region of interest.
Figure 6C:
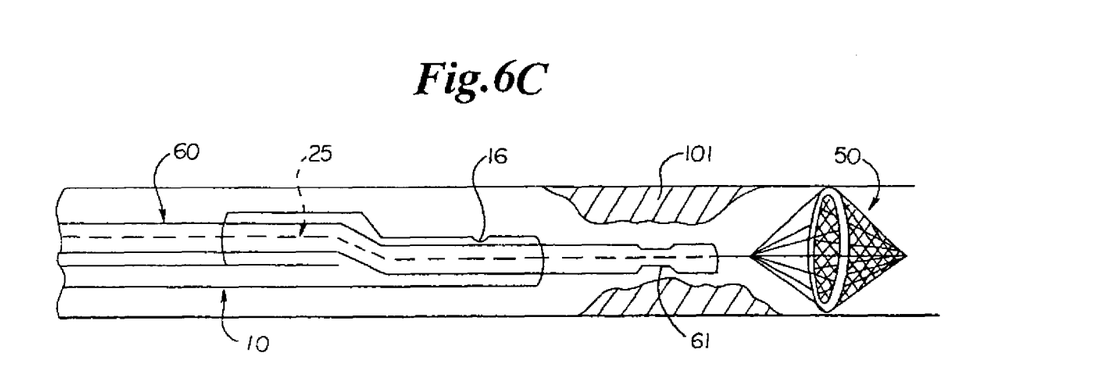
FIG. 6C depicts an atherectomy device deployed within the region of interest using the rapid exchange sheath of FIG. 5C.

In using the embodiment of FIG. 5C in treating a vascular lesion, the guidewire is first inserted through a peripheral vessel and advanced to a region of interest. In FIG. 6A, the proximal end of guidewire 20 is inserted through first opening 15, lumen 11, and second opening 16 of tubular member 10. Support wire 25, which carries filter 50 in a collapsed state, is inserted in lumen 11 prior to insertion of tubular member 10 over guidewire 20. In this way, the steerability of the support wire is not likely to be altered as compared to conventional guidewires since the support wire and the filter are carried within lumen 11. The support wire is less likely to bend, kink, and/or loop around in the vessel, allowing an easy insertion of the filter through a complex vascular lesion. After tubular member 10 is advanced proximal to lesion 101, guidewire 20 is removed as depicted in FIG. 6B. Filter 50 is advanced distal to lesion 101 and expanded to capture embolic material generated during the endovascular procedure. Filter 50 also includes inflation seal 51 which, in an expanded state, maintains uniform contact with the vascular lumen and prevents the filter from displacement in the vessel. Atherectomy catheter 60, which carries atherectomy device 61 on its distal end, is advanced over support wire 25 within lumen 11 to position within lesion 101 as depicted in FIG. 6C. For the design and construction of suitable atherectomy devices the reader is referred to U.S. Pat. No. 5,662,671, incorporated herein by reference in its entirety.

Figure 6D:
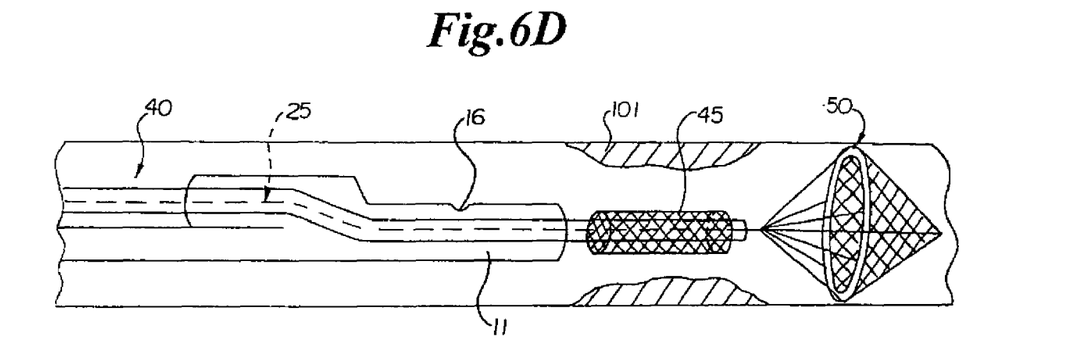
FIG. 6D depicts a stent deployment catheter disposed within a region of interest using the rapid exchange sheath of FIG. 6C.
Figure 6E:
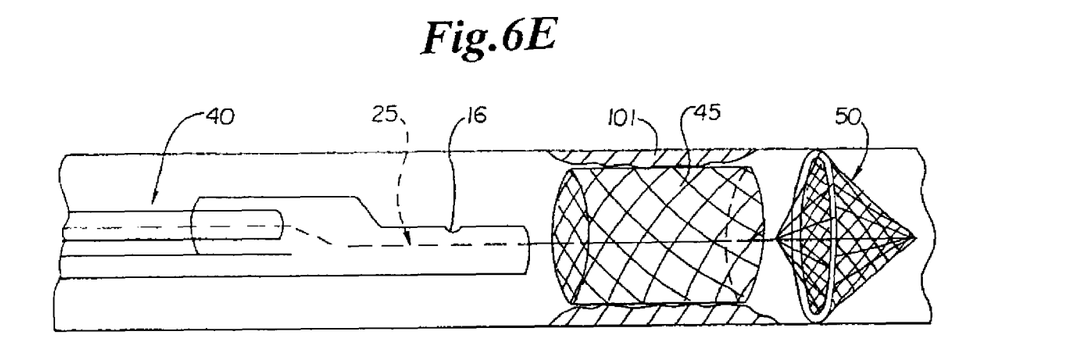
FIG. 6E depicts the stent of FIG. 6D deployed within the region of interest.

After revascularization is achieved by removing the occluding lesion using the atherectomy device of FIG. 6C, atherectomy catheter 60 is removed. Stent deployment catheter 40, which carries stent 45 in a collapsed state, is inserted over support wire 25 and advanced to position within the region of interest as depicted in FIG. 6D. Stent 45 is then expanded within lesion 101 to maintain lumenal patency after atherectomy. In this way, exchange of endovascular devices can be easily achieved without compromising the position of the support wire (which functions as a guidewire for insertion of medical devices) and obviate the need to insert another guidewire. After stent deployment, catheter 40 is withdrawn as depicted in FIG. 6E. Fluid, such as saline or Ringer's lactate, may be infused through lumen 11 to irrigate within lesion 101 or to flush embolic debris into filter 50. The proximal end of lumen 11 may alternatively be attached to suction to aspirate embolic material within region 101. Filter 50 remains expanded during atherectomy and stent deployment to capture embolic debris, thereby minimizing the risk of distal embolization.

Figure 7A:
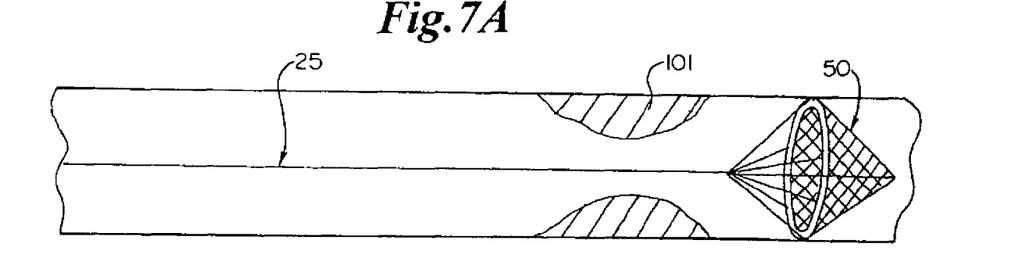
FIG. 7A depicts a support wire deployed within a vascular lesion.
Figure 7B:
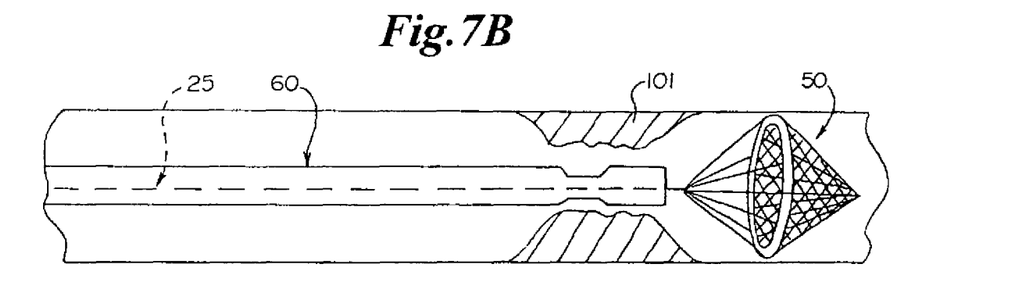
FIG. 7B depicts an atherectomy catheter inserted over the support wire of FIG. 7A and deployed within the vascular lesion.
Figure 7C:
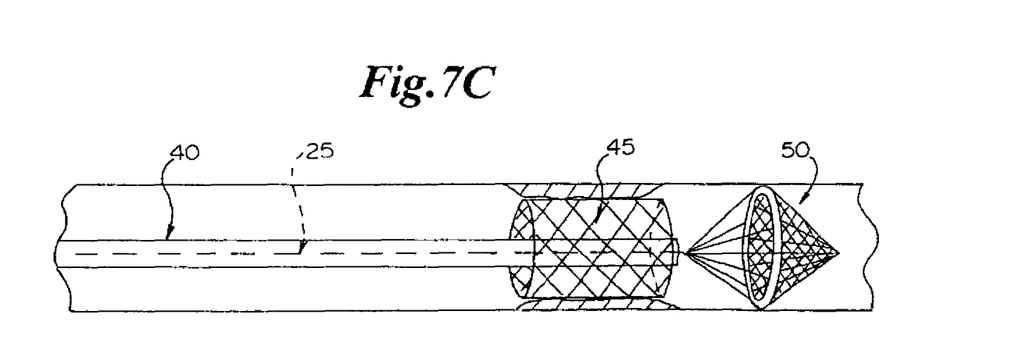
FIG. 7C depicts a stent deployment catheter inserted over the support wire of FIG. 7A and deploying a stent over the vascular lesion.

Alternatively, after filter 50 of FIG. 6B is positioned and expanded downstream lesion 101, the tubular sheath is removed from the vessel as depicted in FIG. 7A. Atherectomy catheter 60 is advanced over support wire 25 to position within lesion 101 as depicted in FIG. 7B. When deployment of stent 45 is desired, catheter 60 is removed and stent deployment catheter 40 is inserted over support wire 25 to position the stent within lesion 101 as depicted in FIG. 7C.

Figure 8:
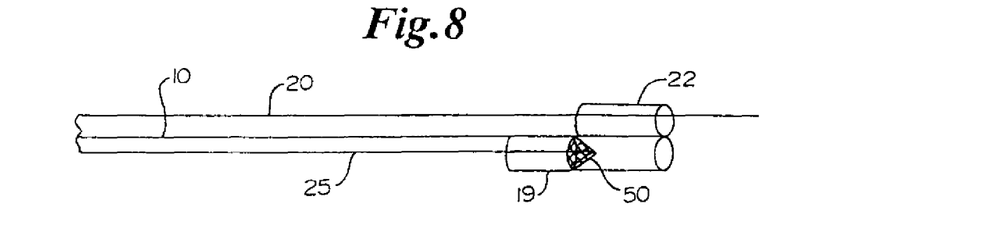
FIG. 8 depicts another embodiment of the rapid exchange sheath for deployment of a catheter according to the present invention.

Another embodiment of a double rapid exchange ("double RX") sheath is depicted in FIG. 8. Sheath 10 comprises RX engagement section 22, a tubular member, at the distal end of the sheath for engagement with, and to track over conventional guidewire 20. A second RX engagement section or containment area 19, also a tubular member, is carried at the distal end of sheath 10 for containment and deployment of filter wire 25, or other device. The body of sheath 10 comprises the majority of the length of the sheath.

Figure 8A:
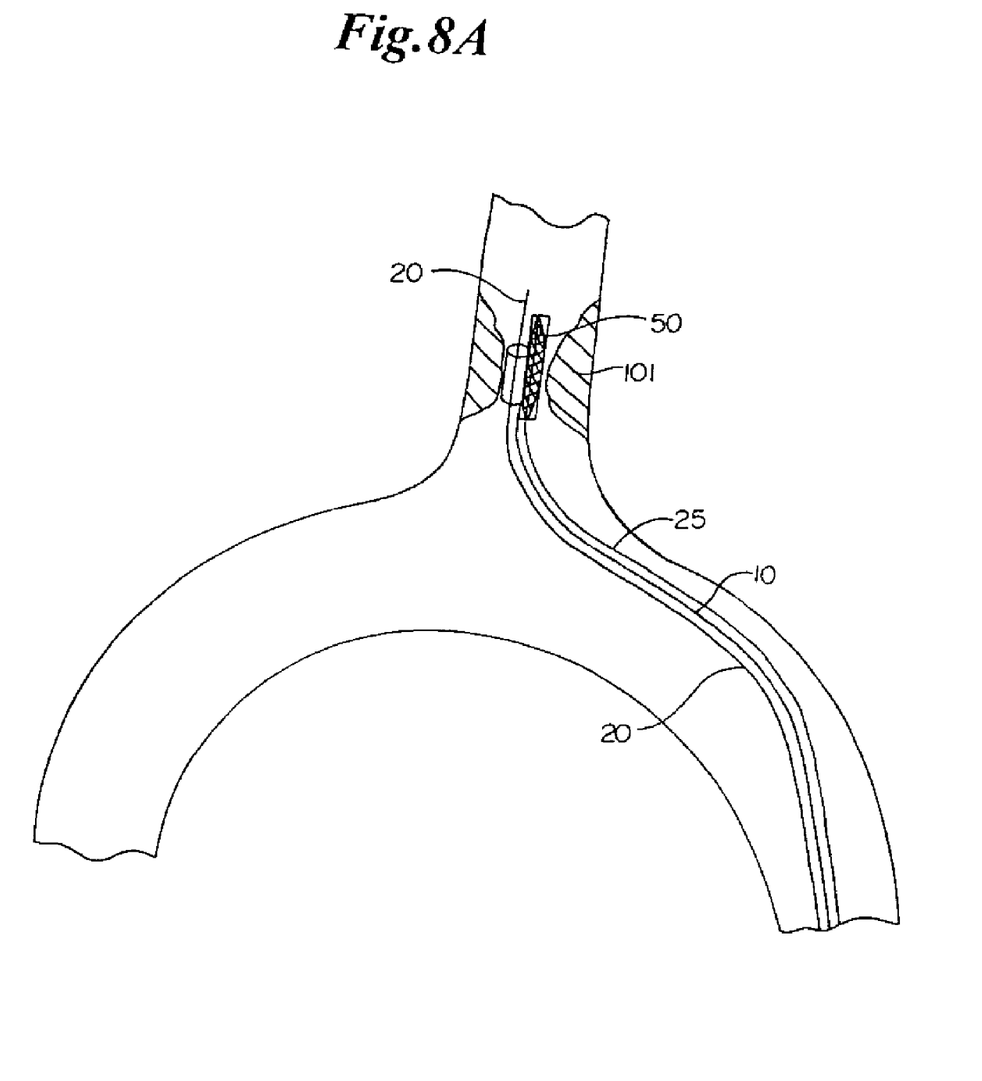
FIG. 8A depicts the sheath of FIG. 8 in use within a vessel to carry a filter wire.
Figure 8B:
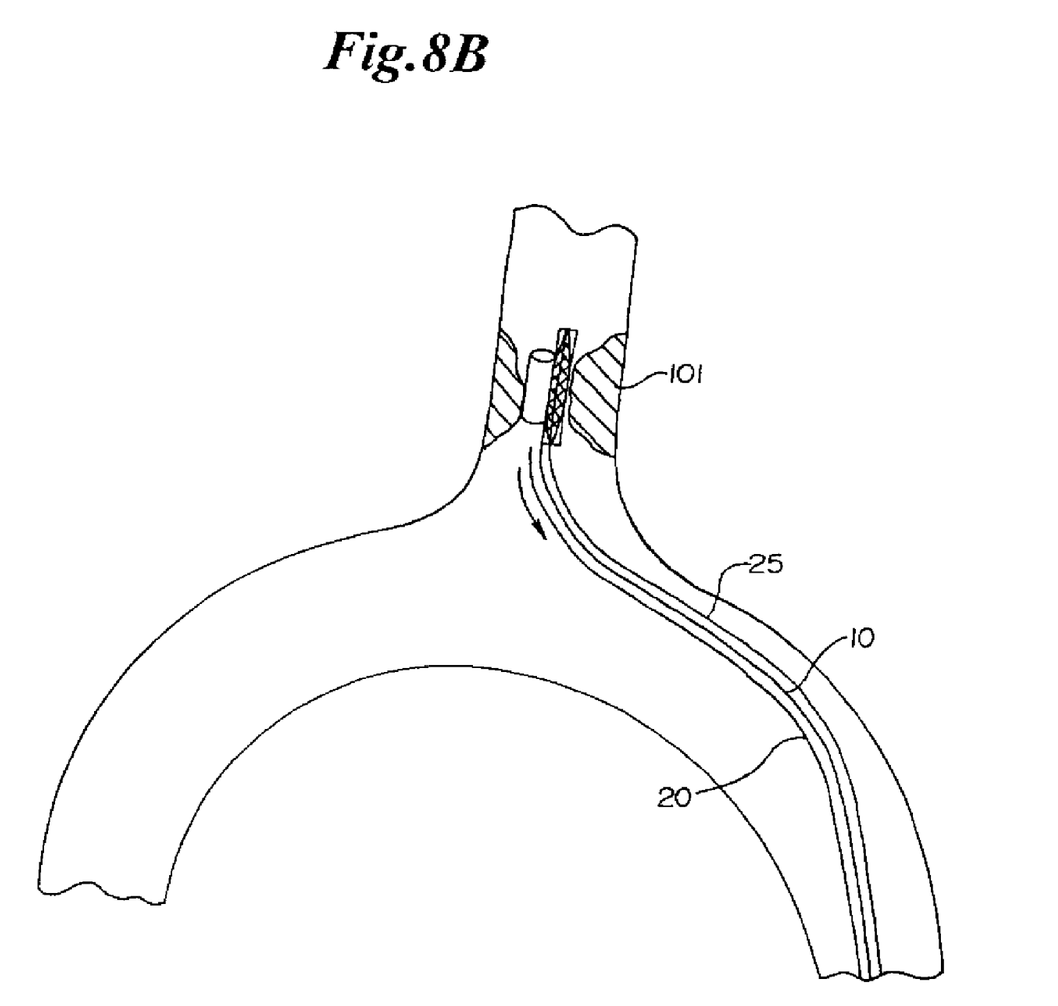
FIG. 8B depicts the sheath of FIG. 8A during removal of the guidewire.
Figure 8C:
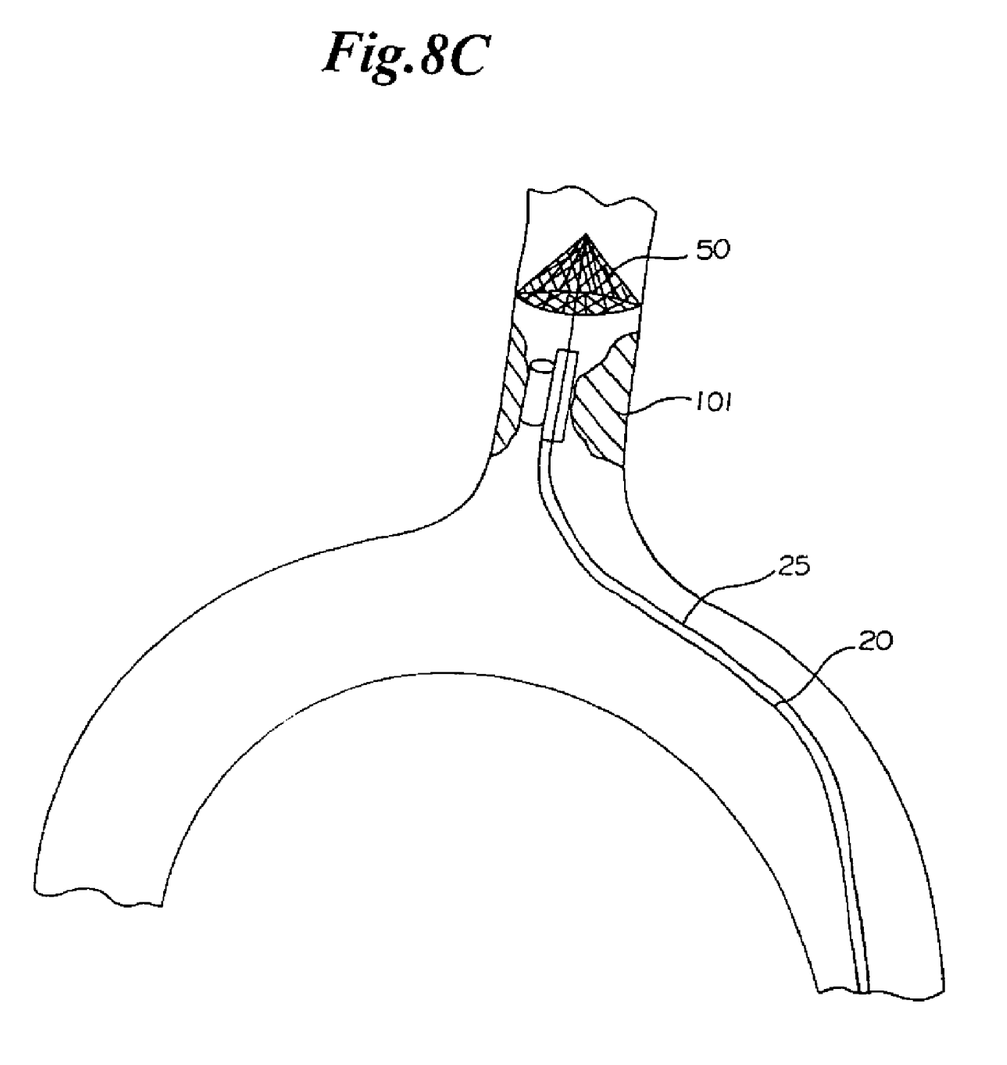
FIG. 8C depicts the sheath of FIG. 8B after filter deployment.
Figure 8D:
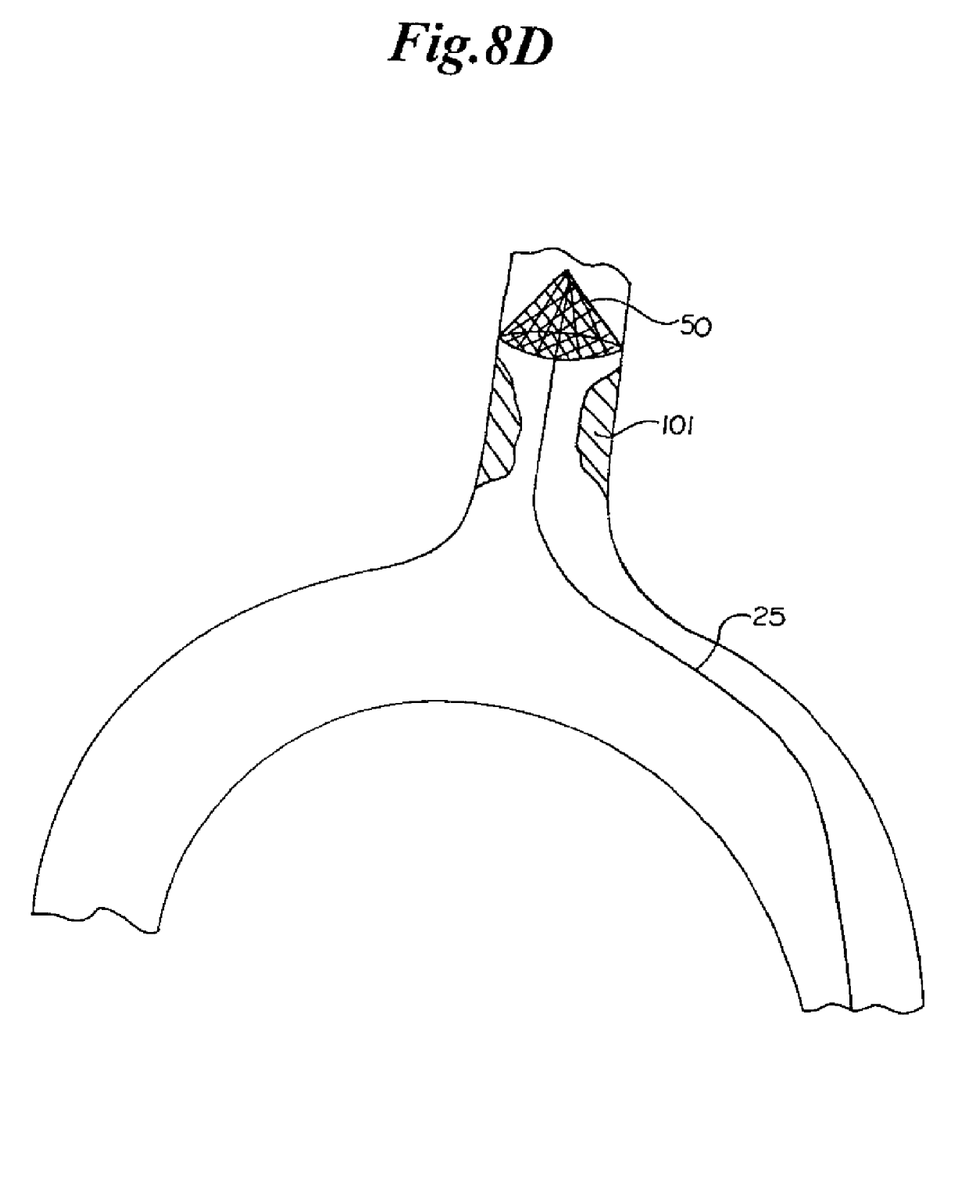
Figure 8E:
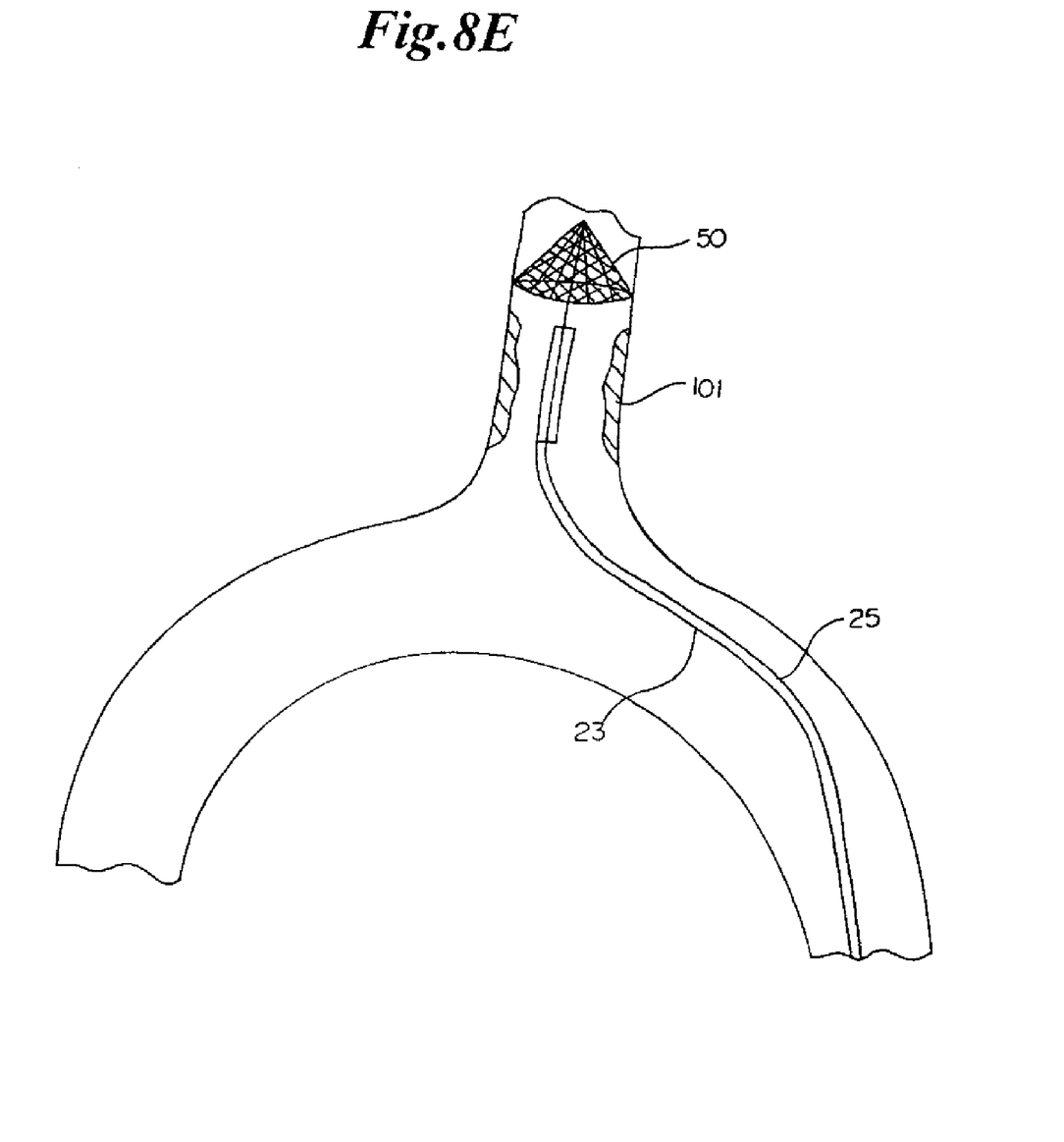
FIG. 8E depicts retrieval by a capture sheath of the filter wire of FIG. 8D.

In use, conventional guidewire 20 is used to gain access to the filter deployment site, lesion 101, as depicted in FIG. 8A. Sheath 10 (with filter wire 25 contained in second RX section 19) is delivered to deployment site 101 over guidewire 20. The conventional guidewire is then withdrawn, as depicted in FIG. 8B, and may then be removed from the patient. The proximal end of filter wire 25 is gripped to maintain position, and sheath 10 is pulled proximal to deploy filter 50, as depicted in FIG. 8C. Alternatively, the filter wire can be pushed distally to deploy the filter. Sheath 10 may then be removed from the patient, as depicted in FIG. 8D. An endoluminal catheter, optionally carrying a therapeutic device (such as an angioplasty catheter, a stent-deployment catheter, an atherectomy catheter, an intravascular ultrasound catheter, a filter catheter, a guidewire, and an aspiration catheter), is then advanced over filter wire 25 with filter 50 deployed. An interventional procedure is then performed on the vessel with filter 50 in place to capture emboli dislodged during the procedure. Recovery of the filter is accomplished with a second, separate sheath 23 with only one RX section for to containment of the filter (i.e., no RX engagement for a conventional guidewire), as depicted in FIG. 8E. A primary advantage of the double RX design described herein is that both the conventional guidewire and the filter wire or support wire can be of minimal length, and control of both wires is maximized.

The length of the sheath will generally be between approximately 40 and 200 centimeters, preferably between approximately 60 and 80 centimeters. The inner diameter of the sheath will generally be between approximately 0.05 and 1.0 centimeters, and for small vessels preferably approximately 0.07 and 0.2 centimeters, whereas for large vessels preferably approximately 0.3 and 0.8 centimeters. The length of the guidewire will generally be between approximately 30 and 300 centimeters, preferably between approximately 70 to 200 centimeters. The length of the support wire will generally be between approximately 30 and 300 centimeters, preferably between approximately 70 to 200 centimeters. The outer diameter of the guidewire will generally be between approximately 0.008 and 0.038 inches, preferably approximately 0.010 and 0.014 inches. The diameter of the expansion frame on the filter device will be capable of expansion to an outer diameter of at least 0.2 cm, more preferably at least 1.5 cm, more preferably at least 2 cm, more preferably at least 2.5 cm, more preferably at least 3 cm, more preferably at least 3.5 cm, more preferably at least 4 cm, more preferably at least 4.5 cm, more preferably at least 5 cm, more preferably at least 5.5 cm, more preferably at least 6 cm. For carotid use, the diameter of the expansion frame on the filter device will be capable of expansion to an outer diameter of 5-7 mm. These ranges cover suitable diameters for a variety of arteries and veins, and for both pediatric use and adult use. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for purposes of clarity of understanding, been described in some detail by way of illustration and example, it will be obvious that certain changes and modifications may be practiced which will still fall within the scope of the appended claims. It will also be understood that each feature of each embodiment discussed herein, and of each reference cited herein, can be used in combination with the features of any other embodiment.

What is claimed is:

1. A sheath for deployment of a medical device comprising:
    an elongate tubular member having a proximal end, a distal end, and a lumen therebetween;
    a first opening in the lumen at the distal end of the tubular member;
    a second opening in the lumen proximal the distal end of the tubular member;
    a third opening in the lumen proximal the second opening in the lumen and distal the proximal end;
    a guidewire that passes through the second opening, through the lumen of the elongate tubular member, and through the first opening; and
    a support wire having a proximal end and a distal end, the support wire being positioned within at least a portion of the lumen of the elongate tubular member.

2. The sheath of claim 1 wherein the support wire is adapted to receive an endoluminal medical device.

3. The sheath of claim 1, wherein the second opening is a short distance proximal to the distal end and the third opening is a short distance proximal to the second opening.

4. The sheath of claim 1, wherein the second opening is located 50 centimeters or less from the distal end.

5. The sheath of claim 1, wherein the second opening is located 10 centimeters or less from the distal end.

6. A sheath for deployment of a medical device having a first outer diameter in a first, closed state and a second outer diameter in a second, expanded state, comprising:
    an elongate tubular member having a proximal end, a distal end, and a lumen therebetween, the elongate tubular member having a first opening from the lumen at the distal end, a second opening from the lumen proximal to the distal end, and a third opening from the lumen proximal of the second opening and distal of the proximal end of the tubular member, the openings defining points at which the lumen opens to an environment surrounding the sheath;
    a guidewire that passes through the first opening, through the lumen of the elongate tubular member, and through the second opening; and
    an elongate member including an expandable filter, the elongate member at least partially disposed in the lumen and passing through the third opening.

7. The sheath of claim 6, wherein the sheath is a rapid exchange sheath.

8. The sheath of claim 6, wherein the second opening is a short distance proximal to the distal end.

9. The sheath of claim 6, wherein the expandable filter is mounted on a distal end of the elongate member.

10. The sheath of claim 9, wherein the elongate member and filter are positioned within the lumen of the elongate tubular member.

11. The sheath of claim 6, further comprising an endoluminal medical device.

12. The sheath of claim 6, wherein the proximal end of the elongate tubular member includes a hemostatic valve.

13. The sheath of claim 11, wherein the endoluminal medical device is selected from the group consisting of an angioplasty catheter, a stent-deployment catheter, an atherectomy catheter, an intravascular ultrasound catheter, a filter catheter, a guidewire, and an aspiration catheter.

14. The sheath of claim 6, wherein the second opening is located 10 centimeters proximal from the distal end.

* * * * *